United States Patent [19]

Rasmusson et al.

[11] Patent Number: 5,120,742
[45] Date of Patent: Jun. 9, 1992

[54] 17 β-ACYL-4-AZA-5 α-ANDROST-1-ENE-3-ONES AS 5 α-REDUCTASE INHIBITORS

[75] Inventors: Gary H. Rasmusson, Watchung; Glenn F. Reynolds, Westfield, both of N.J.

[73] Assignee: Merck & Co., Inc., Rahway, N.J.

[21] Appl. No.: 683,520

[22] Filed: Apr. 9, 1991

Related U.S. Application Data

[63] Continuation of Ser. No. 396,183, Aug. 21, 1989, abandoned, which is a continuation-in-part of Ser. No. 363,567, Jun. 8, 1989, abandoned, which is a continuation of Ser. No. 129,335, Dec. 3, 1987, Pat. No. 4,859,681, which is a continuation of Ser. No. 800,624, Nov. 21, 1985, abandoned, which is a continuation of Ser. No. 584,061, Feb. 27, 1984, abandoned.

[51] Int. Cl.$^5$ .................... A61K 31/58; C07J 73/00
[52] U.S. Cl. ...................................... 514/284; 546/77
[58] Field of Search ......................... 546/77; 514/284

[56] References Cited

U.S. PATENT DOCUMENTS

| | | | |
|---|---|---|---|
| 2,227,876 | 1/1941 | Bolt | 546/77 X |
| 3,239,417 | 3/1966 | DiTullio et al. | 514/284 |
| 3,264,301 | 8/1966 | Doorenbos et al. | 546/77 |
| 3,285,918 | 11/1966 | Doorenbos et al. | 544/245 |
| 4,220,775 | 9/1980 | Rasmusson et al. | 546/77 |
| 4,377,584 | 3/1983 | Rasmusson et al. | 514/284 |
| 4,732,897 | 3/1988 | Cainelli et al. | 514/222 |
| 4,760,071 | 7/1988 | Rasmusson et al. | 514/284 |
| 4,845,104 | 7/1989 | Carlin et al. | 514/284 |
| 4,859,681 | 8/1989 | Rasmusson et al. | 514/284 |
| 5,049,562 | 9/1991 | Rasmusson et al. | 514/284 |

FOREIGN PATENT DOCUMENTS

| | | |
|---|---|---|
| 970692 | 7/1975 | Canada . |
| 155096 | 9/1985 | European Pat. Off. . |
| 0314199 | 5/1989 | European Pat. Off. ......... 546/77 |
| 1465544 | 11/1965 | France . |

OTHER PUBLICATIONS

Neri et al., *Endo*, vol. 91, No. 2 (1972), pp. 424–437.
Nayfeh et al., *Steroids* 14, (1969), pp. 269–283.
Doorenbos & Solomon, *J. Pharm. Sci.*, 62, 4, pp. 638–640 (1973).
Doorenbos & Brown, *J. Pharm. Sci.*, 60, 8, pp. 1234–1235 (1971).
Doorebos and Kim, *J. Pharm.*, 63, 4, pp. 620–622 (1974).
Rasmusson et al., *J. Med. Chem.* (1986) 29(11): 2298-315.
Brooks et al., *Prostate* (1986)9(1): 65-75.
Brooks et al., *Steroids* (1986) 47 (1): 1-19.
Liang et al., *Endocr.* (1985) 117 (2): 571-9.
Rasmusson et al., *J. Med. Chem.* (1984) 27 (12): 1690-701.
*J. Org. Chem.*, vol. 46, No. 7, pp. 1442-1446 (Jul. 1981) by T. G. Back.
*Chem. Abstracts*, vol. 95, 109056j, by T. Liang et al. Sep. 28, 1981.
*JNCI*, vol. 74, No. 2, pp. 475-481, Feb. 1985.
*The Prostate*, vol. 10, pp. 189-197 (1987), by G. L. Andriole et al.
*J. Endocr.*, vol. 57, pp. 111-121 (1973) by K. D. Bingham et al.
*Toxicol. Appl. Pharmacol.*, vol. 103, pp. 222-227, by G. L. Kedderis et al. Feb. (1987).

*Primary Examiner*—Diana Rivers
*Attorney, Agent, or Firm*—Robert J. North; Charles M. Caruso

[57] ABSTRACT

17β-Acyl-4-aza-5α-Androst-1-end-3-ones of the formula:

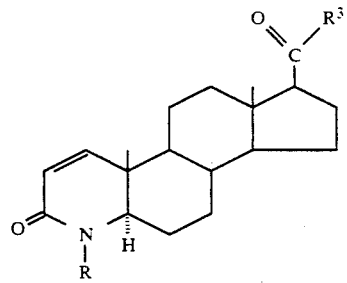

wherein
R is selected from hydrogen, methyl and ethyl and R$^3$ is cycloalkyl of from 4-8 carbons;

and pharmaceutical formulation of the above compounds are active as testosterone 5α-reductase inhibitors and thus are useful for treatment of acne, seborrhea, female hirsutism, androgenic alopecia, prostatic carcinoma and benign prostatic hypertrophy.

7 Claims, No Drawings

17 β-ACYL-4-AZA-5 α-ANDROST-1-ENE-3-ONES AS 5 α-REDUCTASE INHIBITORS

CROSS-REFERENCE TO RELATED APPLICATIONS

This is a continuation of application Ser. No. 07/396,183, filed Aug. 21, 1989, now abandoned, which is a continuation-in-part of U.S. Ser. No. 363,567, filed Jun. 8, 1989, abandoned, which in turn is a continuation of U.S. Ser. No. 129,335, filed Dec. 3, 1987, U.S. Pat. No. 4,859,681, which in turn is a continuation of U.S. Ser. No. 800,624, filed Nov. 21, 1985, now abandoned, which in turn is a continuation of U.S. Ser. No. 584,061, filed Feb. 27, 1984, now abandoned.

BACKGROUND OF THE INVENTION

The present invention is concerned with novel 17β-acyl-4-aza-5α-androst-1-ene-3-one compounds and the use of such compounds as testosterone-5α-reductase inhibitors.

DESCRIPTION OF THE PRIOR ART

It is well known in the art that certain undesirable physiological manifestations, such as acne vulgaris, seborrhea, female hirsutism, and male pattern baldness and benign prostatic hypertrophy, are the result of hyperandrogenic stimulation caused by an excessive accumulation of testosterone or similar androgenic hormones in the metabolic system. Early attempts to provide a chemotherpeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethylisobutyranilide. See Neri et al., *Endo.*, Vol. 91, No1 2 (1972). However, these products, though devoid of hormonal effects, are peripherally active, competing with the natural androgens for receptor sites, and hence have a tendency to feminize a male host or the male fetus of a female host.

It more recently became known in the art that the principal mediator of androgenic activity in some target organs is 5α-dihydrotestosterone, and that it is formed locally in the target organ by the action of testosterone-5α-reductase. It therefore has been postulated and demonstrated that inhibitors of testerone-5α-reductase will serve to prevent or lessen symptoms of hyperandrogenic stimulation. Nayfeh et al., *Sieroids*, 14, 269 (1969) demonstrated in vitro that methyl 4-androsten-3-one-17β-carboxylate was a testosterone-5α-reductase inhibitor. Then Voight and Hsia, *Endocrinology*, 92, 1216 (1973), Canadian Pat. No. 970,692, demonstrated that the above ester and the parent free acid, 4-androsten-3-one-17β-carboxylic acid are both active inhibitors of testosterone-5α-reductase in vitro. They further demonstrated that topical application of either testosterone or 5α-dihydrotestosterone caused enlargement of the female hamster flank organ, or androgen dependent sebaceous structure. However, concomitant administration of 4-androsten-3-one-17β-carboxylic acid or its methyl ester inhibited the response elicited by testosterone but did not inhibit the response elicited by 5α-dihydrotestosterone. These results were interpreted as indicating that the compounds were antiandrogenic by virtue of their ability to inhibit testosterone-5α-reductase.

A number of 4-aza steroid compounds are known. See, for example, U.S. Pat. Nos. 2,227,876; 3,239,417; 3,264,301; and 3,285,918; French Pat. No. 1,465,544; Doorenbos and Solomons, *J. Pharm. Sci.* 62, 4, pp. 638–640 (1973); Doorenbos and Brown, *J. Pharm. Sci.*, 60, 8, pp. 1234–1235 (1971); and Doorenbos and Kim, *J. Pharm. Sci.*, 63, 4, pp. 620–622 (1974).

In addition U.S. Pat. Nos. 4,377,584 and 4,220,775 of Rasmusson et al. describe a group of 4-aza-5α-17β-substituted-5α-androsten-3-ones which are said to be useful in the treatment of hyperandrogenic conditions. However, none of the cited references suggest that any of the novel 17β-acyl-4-aza-5α-androst-1-ene-3-ones of the present invention would have utility as highly potent testosterone-5-reductase inhibitors.

DESCRIPTION OF THE INVENTION

The present invention is concerned with novel 17β-acyl-4-aza-5α-androst-1-ene-3-one compounds, processes for their preparation, pharmaceutical formulations comprising the novel compounds as active ingredients and methods of inhibiting testosterone-5α-reductase and of treating hyperandrogenic conditions with the novel compounds or their pharmaceutical formulations.

The present invention is concerned with 17β-acyl-4-aza-5α-androst-1-ene-3-one compounds of the formula:

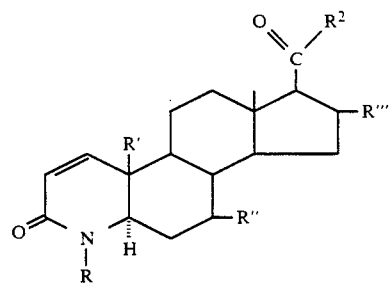

wherein

R is selected from hydrogen, methyl and ethyl; and $R^2$ is a monovalent radical selected from straight and branched chain alkyl of from 1-12 carbons, or monocyclic aryl optionally containing 1 or more lower alkyl substituents of from 1-2 carbon atoms and/or 1 or more halo (Cl or Br) substituents, aralkyl selected from benzyl and phenethyl and heterocyclic selected from 2- or 4-pyridyl, 2-pyrrolyl, 2-furyl or thiophenyl and R', R" and R'" are each selected from hydrogen and methyl.

A preferred embodiment of the novel compounds of our invention is represented by the formula:

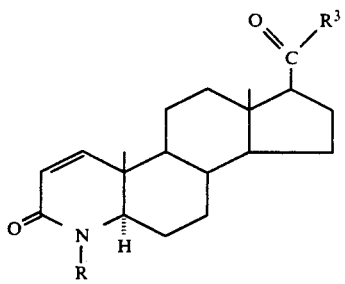

wherein
R is hydrogen, methyl or ethyl, and
$R^3$ is branched chain alkyl or cycloalkyl of from 4–8 carbons.

Representative compounds of the present invention include the following:

17β-(t-butylcarbonyl)-4-aza-4-methyl-5α-androst-1-ene-3-one;
17β-(isobutylcarbonyl)-4-aza-4-methyl-5α-androst-1-ene-3-one;
17β-(isooctylcarbonyl)-4-aza-4-methyl-5α-androst-1-ene-3-one;
17β-(n-octylcarbonyl)-4-aza-4-methyl-5α-androst-1-ene-3-one;
17β-(1,1-diethylbutylcarbonyl)-4-aza-4-methyl-5α-androst-1-ene-3-one;
17β-(neopentylcarbonyl)-4-aza-4-methyl-5α-androst-1-ene-3-one;
17β-(tert-amylcarbonyl)-4-aza-4-methyl-5α-androst-1-ene-3-one;
17β-(tert-hexylcarbonyl)-4-aza-4-methyl-5α-androst-1-ene-3-one;
17β-(5-butylcarbonyl)-4-aza-4-methyl-5α-androst-1-ene-3-one;

and the corresponding compounds wherein the 4-methyl substituent is replaced in each of the above named compounds by a hydrogen or an ethyl radical.

Also included as representative compounds are any of the above indicated compounds having the alkyl of the alkyl carbonyl substituent replaced by a methyl-, ethyl-, propyl-, i-propyl-, butyl-, phenyl-, 2-, 3- or 4-tolyl-, xylyl-, 2-bromo- or 2-chlorophenyl-, 2,6-dichloro- or a 2,6-dibromophenyl carbonyl substituent or a heterocyclic substituent selected from 2 or 4-pyridyl, 2-pyrrolyl, 2-furyl or 2-thiophenyl.

Additional representative compounds are

17β-(cyclobutylcarbonyl)-4-aza-5α-androst-1-ene-3-one;
17β-(cyclopentylcarbonyl)-4-aza-5α-androst-1-ene-3-one;
17β-(cyclohexylcarbonyl)-4-aza-5α-androst-1-ene-3-one;
17β-(cycloheptylcarbonyl)-4-aza-5α-androst-1-ene-3-one;
17β(cyclooctylcarbonyl)-4-aza-5α-androst-1-ene-3-one;

and the above compounds wherein the 4-hydrogen substituent is replaced by a 4-methyl substituent.

The novel compounds of formula I of the present invention are prepared by a method starting with the known steroid ester of the formula:

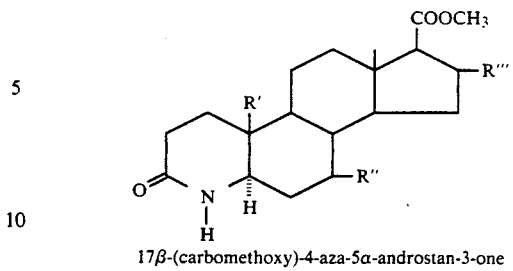

17β-(carbomethoxy)-4-aza-5α-androstan-3-one which includes the stages of (1) dehydrogenating said starting material to produce the corresponding compound containing a double bond in the 1,2-position of the A-ring, (2) converting the 17-carbomethoxy substituent into a 17β-acyl substituent and, if desired (3) alkylating the A-ring nitrogen to introduce 4-methyl or 4-ethyl substituents into the A-ring. In carrying out the process of the present invention, it is essential that stage (1) dehydrogenation of the 1,2-position of the steroid A-ring be carried out using a 4-aza-5α-androsten-3-one compound having no substituent other than hydrogen attached to the A-ring nitrogen. Stage (2) may consist of one or more chemical steps and if desired may take place before stage (1) or following stage (1) or stage (3).

In accordance with the process of the present invention, the products of our invention are formed by (1) heating a 17β-alkoxycarbonyl-4-aza-5α-androstan-3-one compound III with a dehydrogenating agent such as benzeneseleninic anhydride in refluxing chlorobenzene to form a 17β-alkoxycarbonyl-4-aza-5α-androst-1-en-3-one (IV), (2) the formed 5α-androst-1-en-3-one compound from step (1) is reacted with sodium hydride and under anhydrous conditions in a neutral solvent such as dimethylformamide, (2) contacting the resulting reaction mixture with an alkyl (methyl or ethyl) iodide to form the corresponding 17β-alkoxycarbonyl-4-alkyl-4-aza-5α-androst-1-en-3-one (V), (3) subsequently hydrolyzing said with a strong base such as aqueous methanolic potassium hydroxide at the reflux temperature, followed by acidification and isolation of the resulting steroidal acid, 17β-carboxy-4-alkyl-4-aza-5α-androst-1-en-3-one (VI), (4) said steroidal acid is then converted to its corresponding 2-thiopyridyl ester by refluxing with triphenyl phosphine and 2,2'-dipyridyl disulfide in an inert solvent and the product 17β-(2-pyridylthiocarbonyl)-4-alkyl-4-aza-5α-androst-1-en-3-one (VII) is isolated by chromatography on silica, (5) said pyridylthio ester is then reacted with an $R^2$—Li or an $R^2$MgX (X=Cl, Br) compound such as sec-butylmagnesium chloride in tetrahydrofuran to form the desired product 17β-(sec-butylcarbonyl)-4-alkyl-4-aza-5α-androst-1-en-3-one (VIII) which is isolated by chromatography on silica gel. When the previous reaction is carried out using an $R^2$MgX or, an $R^2$—Li compound in place of sec-butylmagnesium chloride, the corresponding 17β-(acyl)-4-alkyl-4-aza-5α-androst-1-en-3-one is prepared wherein acyl is $R^2$ carbonyl.

In accordance with the process of our invention, the corresponding 17β-acyl-4-aza-5α-androst-1-en-3-one XV is readily prepared from the 17β(alkoxycarbonyl)-4-aza-5α-androsten-3-one (IV) by repeating the above series of reaction steps but omitting step 2 hereinabove, i.e., treatment of the 4-aza-5α-androst-1-en-3-one with sodium amide followed by methyl or ethyl iodide.

In accordance with a further alternate process of preparing the compounds of our invention, having only hydrogen as the sole substituent on the ring A-nitrogen, the Δ' double bond in the A-ring is introduced as the last step of the process. Thus, a 17β-alkoxycarbonyl-4-aza-5α-androstan-3-one (III) is hydrolyzed to the corresponding steroidal acid, 17β-carboxy-4-aza-5α-androstan-3-one, (IX) which, in turn, is converted to the corresponding thiopyridyl ester, 17β-(2-pyridylthiocarbonyl)-4-aza-5α-androstan-1-one (X) followed by treatment of the ester with an R²MgX or R²LL compound wherein R² is as defined hereinabove to form a 17β-(acyl)-4-aza-5α-androstan-3-one (XI) which is dehydrogenated as previously described to produce compound XIV, 17β-(acyl)-4-aza-5α-androst-1-en-3-one.

In an additional alternative procedure for making the compounds of formula II, when the starting material is an ester, particularly methyl ester as shown in formula III-V in the schematic, reaction with a Grignard reagent gives the ketone corresponding to the moiety associated with the Grignard reagent.

The 16 methyl derivative wherein R''' is methyl are prepared from known 16-methyl-17-acyl-4-methyl-4-aza-5α-androstan-3-ones, e.g. 4,16β-dimethyl-17β-acetyl-4-aza-5α-androstan-1-en-3-one by known dehydrogenation procedures for 4-methyl-4-aza compounds to produce the corresponding 4,16β-dimethyl-17β-acetyl-4-aza-5α-androst-1-ene-3-one.

The above reactions are schematically represented in the following structural outline:

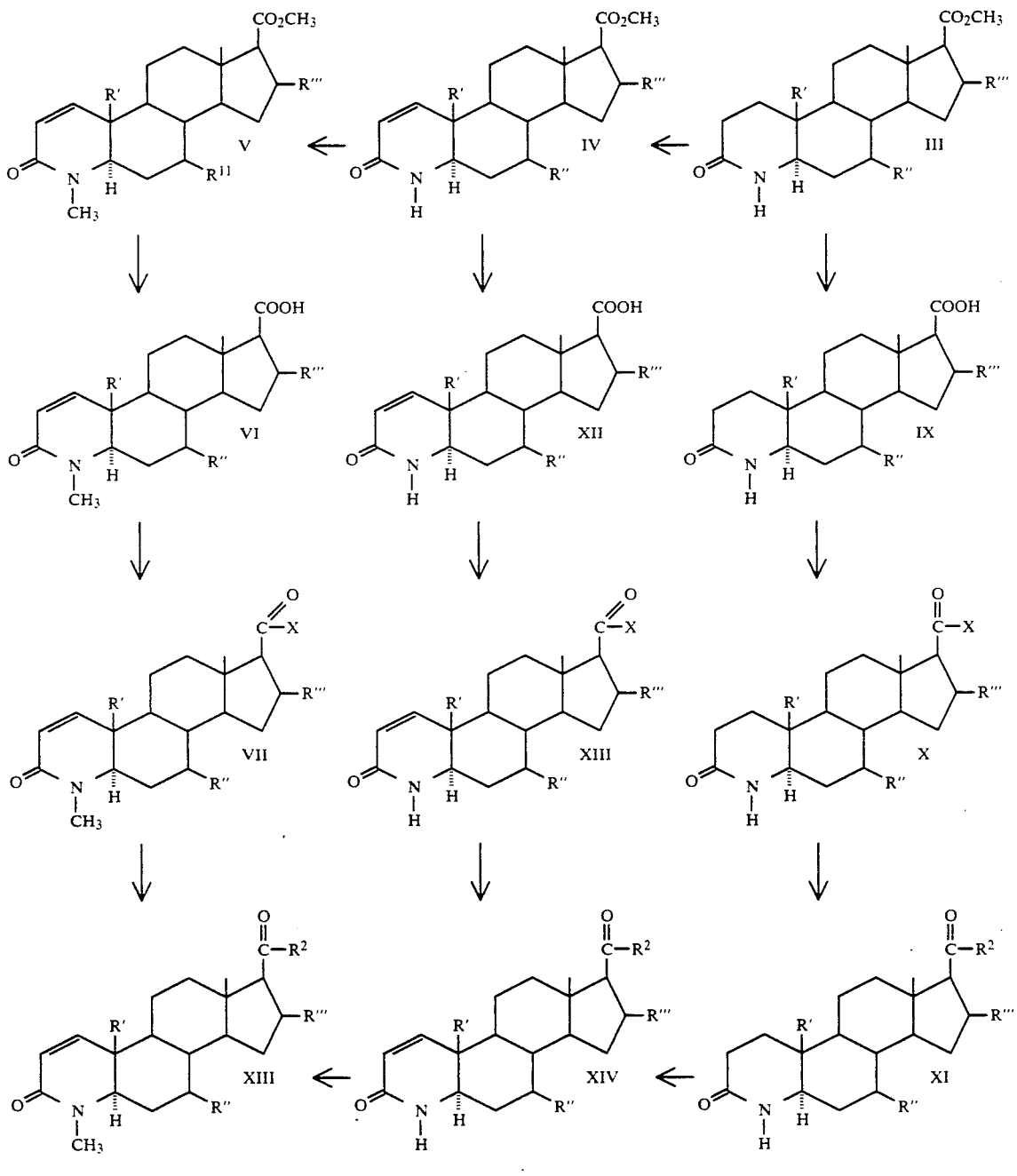

X is 2-pyridylthio wherein X is a pyridylthio substituent and R² is defined as hereinabove, including R3 substituents.

The compounds of the present invention, prepared in accordance with the method described above, are, as already described, potent anti-androgens by virtue of their ability to specifically inhibit testosterone-5α-reductase.

Accordingly, the present invention is particularly concerned with providing a method treating the hyperandrogenic conditions of acne vulgaris, seborrhea, and female hirsutism by topical administration, and a method of treating all of the above conditions as well as benign prostatic hypertrophy, by parenteral administration, of the novel compounds of the present invention.

The present invention is thus also concerned with providing suitable topical and parenteral pharmaceutical formulations for use in the novel methods of treatment of the present invention.

The compositions containing the compounds of the present invention as the active ingredient for use in the treatment of benign prostatic hypertrophy can be administered in a wide variety of therapeutic dosage forms in conventional vehicles for systemic administration, as for example, by oral administration in the form of tablets, capsules, solutions, or suspensions, or by intravenous injection. The daily dosage of the products may be varied over a wide range varying from 50 to 2,000 mg. The compositions are preferably provided in the form of scored tablets containing 5, 10, 25, 50, 100, 150, 250, and 500 milligrams of the active ingredient for the symptomatic adjustment of the dosage to the patient to be treated. An effective amount of the drug is ordinarily supplied at a dosage level of from about 0.005 mg to about 50 mg/kg of body weight per day. Preferably the range is from about 0.01 mg to 5 mg/kg of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calcium phosphate, lactose, corn starch or magnesium stearate. The liquid forms in suitably flavored suspending or dispersing agents such as the synthetic and natural gums, for example, tragacanth, acacia, methylcellulose and the like. Other dispersing agents which may be employed include glycerin and the like. For parenteral administration sterile suspensions and solutions are desired. Isotonic preparations which generally contain suitable preservative are employed when intravenous administration is desired.

For the treatment of acne vulgaris, seborrhea, female hirsutism, the compounds of the present invention are administered in the formula of pharmaceutical composition comprising the active compound in combination with a pharmacologically acceptable carrier adapted for topical administration. These topical pharmaceutical compositions may be in the form of a cream, ointment, gel or aerosol formulation adapted for application to the skin. These topical pharamaceutical compositions containing the compounds of the present invention ordinarily include about 0.1% to 15%, preferably about 5%, of the active compound, in admixture with about 95% of vehicle.

The method of preparing the novel compounds of the present invention, already described above in general terms, may be further illustrated by the following examples.

EXAMPLE 1

22-Methyl-4-aza-21-nor-5α-chol-1-ene-3,20-dione

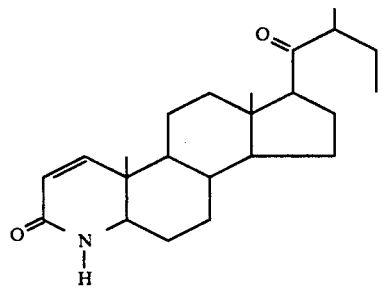

To a solution of 7.2 g of S-(2-pyridyl)-3-oxo-4-aza-5α-androst-1-ene-17β-thiocarboxylate in 288 ml of tetrahydrofuran was added at −78° C. 33.6 ml of 1.3M S-butylmagnesium chloride. After 30 minutes at −78° C. the solution came to room temperature and was treated with saturated aqueous NaCl solution. The product was extracted into dichloromethane and was washed with saturated aqueous NaCl solution and 10% aqueous NaOH solution, then dried and concentrated. The residue was eluted through 430 g of silica gel with 9:1 dichloromethane-acetone to give 4.5 g of the product, m.p. 246°-249° C.

When the procedure is repeated using the following reagents, the indicated product is obtained.

| Starting Material | Reagent | Product |
|---|---|---|
| S-(2-pyridyl)3-oxo-4-aza-5α-androst-1-en-17β-thiocarboxylate | 2-pyrrolyl magnesium chloride | 17β-(2-pyrrolyl-carbonyl)-4-aza-5α-androst-1-en-3-one m.p. 294-296° C. |
| S-(2-pyridyl)3-oxo-4-methyl-5α-androst-1-en-17β thiocarboxylate | sec-butyl magnesium chloride | 4,22-dimethyl-4-aza-21-nor-5α-chol-1-ene-3,20-dione m.p. 134-136° C. |
| S-(2-pyridyl)3-oxo-4-methyl-4-aza-5α-androst-1-en-17β-thio-carboxylate | 2-pyrrolyl magnesium chloride | 4-methyl-17β-(2-pyrrolylcarbonyl)-4-aza-5α-androst-1-en-3-one m.p. 234-238° C. |
| S-(2-pyridyl)3-oxo-4-aza-5α-androst-en-17β-thiocarboxylate | isobutyl magnesium chloride | 23-methyl-4-aza-21-nor-5α-cholane-3,20-dione m.p. 220-222° C. |

EXAMPLE 2

22-Methyl-4-aza-21-nor-5α-chol-1-ene-3,20-dione

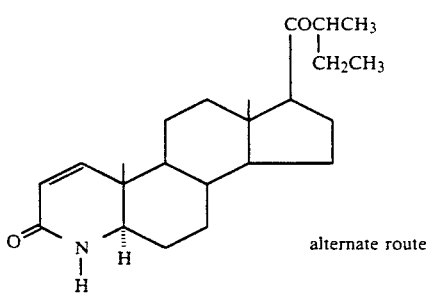

alternate route

A solution of 21 g of 22-methyl-4-aza-21-nor-5α-cholane-3,20-dione (Step1) and 29.49 g of benzeneseleninic anhydride in 552 ml of chlorobenzene was refluxed with water separation for 4 hours. The mixture was concentrated and the residue was redissolved in dichloromethane. After washing with 10% aqueous sodium hydroxide, then 10% hydrochloric acid and saturated aqueous sodium choride the solution was dried and concentrated to 45 g of yellow residue. This was chromatographed on 1.5 kg of silica gel packed in dichloromethane and eluted with ethyl acetate to give 10.6 g of the product, m.p. 248°–251° C.

When the procedure is repeated using 23-methyl-4-aza-21-nor-5α-cholane-3,20-dione as starting material the product obtained is 23-methyl-4-aza-21-nor-5α-chol-1-ene-3,2-dione, m.p. 283°–286° C.

EXAMPLE 3

17β-(cyclohexylcarbonyl)-4-aza-5α-androst-1-ene-3-one

To a suspension of 34.8 g of the thiopyridyl ester in 700 ml of anhydrous THF was added at −65 degrees C. 130 ml of a 2M ether solution of cyclohexyl magnesium chloride over a period of 20 minutes. After stirring at −70 degrees C. for 60 minutes the solution was warmed and stirred at −10 degrees C. for 60 minutes. The mixture was diluted with 500 ml of dichloromethane and then dropwise with 250 ml of 2N HCl. After dilution with 1000 ml of dichloromethane, the phases were seperated and the organic layer was treated sequentially with water, 1N sodium hydroxide, water and saturated sodium chloride solution. The organic solution was decolorized with charcoal, filtered and concentrated to a residue which was crystallized from ethyl acetate to give 28.2 g of the title compound, m.p. 271.5–277 degrees C.

EXAMPLE 3a

The title compound of Example 3 was also prepared by the following procedure.

To a mixture of 150 g of methyl 3-oxo-4-aza-5-alpha-androst-1-ene-17-beta-carboxylate in 2800 ml of anhydrous THF was added with stirring at less than 0 degrees C. internal temperature 678 ml of a 2N ether solution of cyclohexyl magnesium chloride. The solution was then refluxed for 6 hours. The cooled (less than 10 degrees C.) reaction mixture was acidified with 10% HCl solution and was extracted with dichloromethane. The organic layer was washed sequentially with water, saturated NaHCO3 solution and saturated NaCl solution. Drying (MgSO4) and evaporation left 163 g of crude cyclohexyl ketone. Recrystallization from dichloromethane/ethylacetate gave 131 g of the pure material.

M.p. 269–270 degrees C.

|   | % Calc. | Found |
|---|---------|-------|
| N | 3.61    | 3.61  |
| C | 77.37   | 77.37 |
| H | 9.74    | 10.13 |

EXAMPLE 4

17-beta-(cyclopentylcarbonyl)-4-aza-5-alpha-androst-1-ene-3-one

When the procedure of Example 3 or 3a was repeated using suitable reagents, the title compound was obtained:

M.p. 272–273 degrees C.

|   | Calc  | Found |
|---|-------|-------|
| N | 3.66  | 3.78  |
| C | 75.25 | 74.89 |
| H | 9.60  | 9.54  |

EXAMPLE 5

17-beta-(cyclobutylcarbonyl)-4-aza-5-alpha-androst-1-ene-3-one

When the procedure of Example 3 or 3a was repeated using suitable reagents, the title compound was obtained:

M.p. 288–289 degrees C.

|   | % Calc | Found |
|---|--------|-------|
| N | 3.94   | 3.87  |
| C | 77.71  | 78.06 |
| H | 9.36   | 9.61  |

What is claimed is:

1. A compound of the formula:

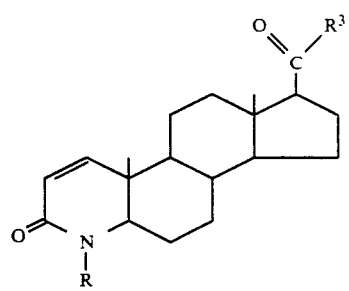

wherein
R is hydrogen, methyl or ethyl; and
$R^3$ is cycloalkyl of from 4–8 carbons.

2. A compound of claim 1 which is

17β-(cyclobutylcarbonyl)-4-aza-5α-androst-1-ene-3-one;
17β-(cyclopentylcarbonyl)-4-aza-5α-androst-1-ene-3-one;
17β-(cyclohexylcarbonyl)-4-aza-5α-androst-1-ene-3-one;

17β-(cycloheptylcarbonyl)-4-aza-5α-androst-1-ene-3-one;

17β-(cyclooctylcarbonyl)-4-aza-5α-androst-1-ene-3-one.

3. A compound of claim 2 wherein the 4-hydrogen substituent is replaced by a 4-methyl substituent.

4. A compound of claim 2 which is 17β-(cyclohexylcarbonyl)-4-aza-5α-androst-1-ene-3-one.

5. A method of treating the hyperandrogenic condition of acne vulgaris, seborrhea, female hirsutism, and benign prostatic hypertrophy comprising administration to a patient in need of such treatment of a therapeutically effective amount of a compound of claim 1.

6. A method of inhibiting testosterone 5α-reductase in a patient in need of such inhibiting treatment, comprising administration to such a patient of a therapeutically effective amount of a compound of claim 1.

7. A pharmaceutical composition for inhibiting testosterone 5-alpha reductase which comprises a pharmaceutically acceptable carrier and an effective amount of a compound of claim 1.

* * * * *